United States Patent [19]

Doi et al.

[11] Patent Number: 4,962,541
[45] Date of Patent: Oct. 9, 1990

[54] PATTERN TEST APPARATUS

[75] Inventors: Hideaki Doi, Yokohama; Yasuhiko Hara, Machida; Akira Sase, Katsuta; Satoshi Shinada, Kamakura, all of Japan

[73] Assignees: Hitachi, Ltd.; Hitachi video engineering, Incorporated, both of Tokyo, Japan

[21] Appl. No.: 154,239

[22] Filed: Feb. 10, 1988

[30] Foreign Application Priority Data

Feb. 27, 1987 [JP] Japan ................................ 62-42671

[51] Int. Cl.⁵ ............................................... G06K 9/62
[52] U.S. Cl. ............................................ 382/30; 382/8; 382/34; 382/51; 382/27
[58] Field of Search .................. 382/30, 34, 8, 54, 22, 382/51, 27; 358/107, 138, 284, 101, 106, 447

[56] References Cited

U.S. PATENT DOCUMENTS 3,791,678 12/1988 Iwase et al. .......................... 382/51
4,665,554 5/1987 Sternberg ............................. 382/27
4,805,224 2/1989 Koezuka et al. ...................... 382/34

FOREIGN PATENT DOCUMENTS 113102 6/1985 Japan .

Primary Examiner—David K. Moore
Assistant Examiner—Michael Razavi
Attorney, Agent, or Firm—Fay, Sharpe, Beall, Fagan, Minnich & McKee

[57] ABSTRACT

Disclosed is a pattern test apparatus for detecting a fault on the basis of comparison/collation between a test reference pattern and a test target pattern, the apparatus being arranged such that a picture element area is defined by a circle with a predetermined radius on a reference matter having at test reference pattern, and when the number of the picture elements located on the reference pattern is larger than the number of the picture elements located outside the reference pattern, a part of the reference pattern corresponding to a picture element located in the center of the circle is deleted. By such an arrangement, the test reference pattern can be made analogous to the real test target pattern regardless of the shape thereof, so that misjudgment of a normal test target pattern for a fault pattern can be prevented.

5 Claims, 9 Drawing Sheets

PATTERN TEST APPARATUS

BACKGROUND OF THE INVENTION

The present invention relates to a pattern test apparatus in which pattern information given by predetermined values such as model patterns of designed data (numerical values) or a photomask used for forming patterns, is reformed or modified, and more particularly, the invention relates to the formation of a loosened reference pattern which is analogous to a practical pattern as a test target.

As the result of treatment, such as exposure, etching or the like, the practical pattern as a target of the test often has its corner portion rounded or often has its line width changed compared with the model pattern as a standard of the test. In the case where the normality of the test pattern is judged from the comparison between the test pattern and the model pattern, if the model pattern without modification is used as a reference pattern, the test pattern may be misjudged to be a poor test pattern though it is so normal that the round of its corner portion or the change of its line width is permissible.

In order to solve the aforementioned problem, in the prior art, the following picture image processing is applied to the model pattern for the purpose of correcting the difference between the model pattern and the practical test pattern to thereby form a processed pattern analogous to the test pattern, as disclosed in JP-A-60-113102.

The prior art picture image processing method is described with reference to the drawing. The method comprises the steps of: calculating the sum value S of the contents (each of which takes the value of "1" when it is contained in a model pattern 24 and each of which takes the value of "0" when it is not contained in the model pattern 24) of outer picture elements as shown by the oblique lines of FIG. 1 in an arrangement 21 of N×N picture elements including a picture element 23 located in a corner portion of a model pattern 24 as the center thereof; comparing the sum value S with at least one predetermined value K; and modifying the content X of the center 23 of the arrangement 21 of N×N picture elements on the basis of the result of the comparison. In the prior art, the model pattern, as to its corner portion and its line portion, is reformed to be analogous to the practical test pattern by use of the aforementioned method.

Figure 1:
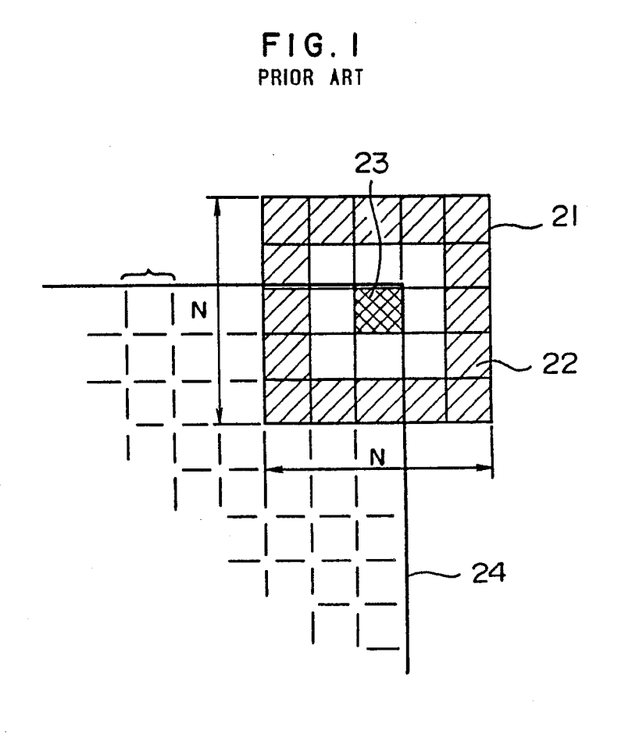
FIGS. 1, 2B, 2C, 3A and 3B are views for explaining a picture image processing technique in the prior art.

In FIG. 1, the inside portion surrounded by the thick solid line to thereby determine the model pattern 24 takes the value of "1", and the outside portion takes the value of "0". If the condition that the center picture element 23 is decided to be "0" when S<K is given (N=5, K=6, S=5), the content of the center picture element 23 is changed from "1" to "0" so that the model pattern 24 is modified to a pattern in which one picture element 23 at its corner has been lost.

Figure 2A:
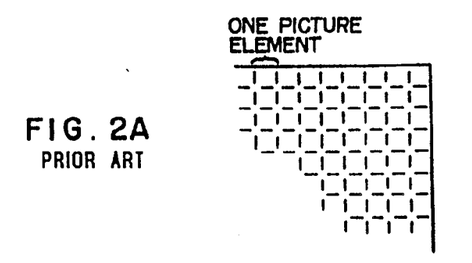
Figure 2B:
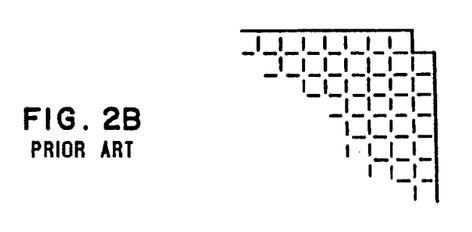

The aforementioned prior art technique has been proposed for the purpose of comparison test between a designed data pattern having its corner portion to form a right angle as shown in FIG. 2A and a test target pattern having its corner portion in which one picture element has been lost as shown in FIG. 2B. However, there has been no consideration about a model pattern having its corner portion rounded over several picture elements as shown in FIG. 2C.

Figure 2C:
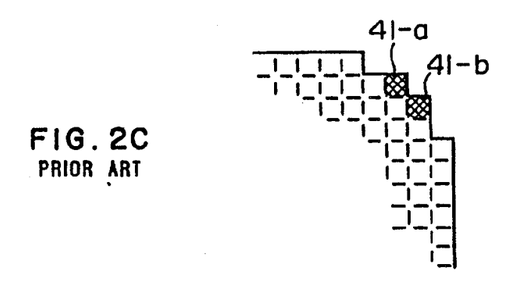

Let the prior art technique be applied to the model pattern of FIG. 2C in the condition of N=5, and let the content X of the center be "0" when the sum value S is more than the predetermined value K. If K is any one of the values 1-7, the corner portion cannot be detected. If K is 8, the corner portion is deformed because the two contents of the picture elements 41-a and 41-b are "0". If K is any one of the values 9-16, the corner portion of the pattern cannot be distinguished from the line portion thereof making processing impossible. Consequently, there is no condition for reforming the model pattern of FIG. 2C suitably. Although the aforementioned problem arises in the case of N=5, the same problem also arises in the other cases.

Because the original purpose of the designed data is to generate a desired pattern on the target objects, the corner portion of the designed data may be rounded over several picture elements corresponding to the desired pattern. Accordingly, it is difficult to reform the model pattern to be analogous to the test target pattern by the prior art technique which is merely applied to the corner portion. Therefore, according to the prior art technique, misjudgment by the test apparatus increases.

Figure 3A:
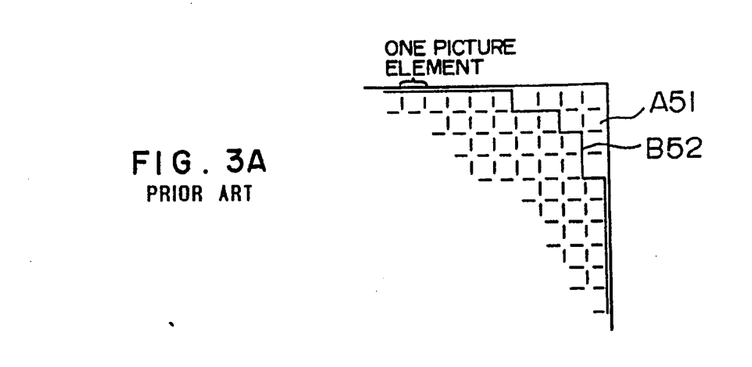
Figure 3B:
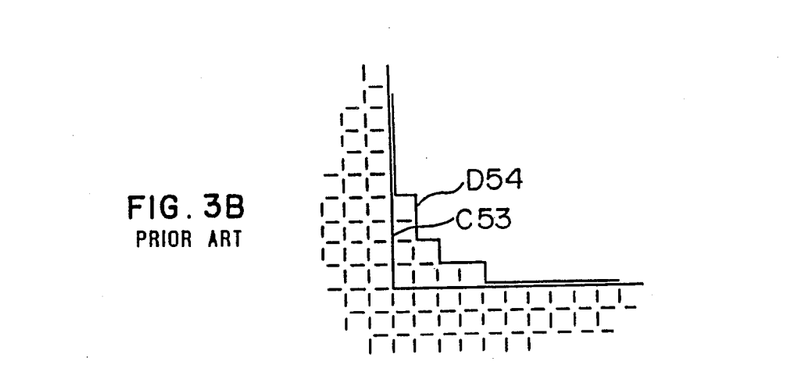

Further, in the practical etching process, the convex corner A51 of the model pattern must be compressed as the convex corner B52 of the test target pattern as shown in FIG. 3A, whereas the concave corner C53 of the model pattern must be expanded as the concave corner D54 of the test target pattern. However, it is theoretically impossible to process the two patterns at once in the prior art technique.

SUMMARY OF THE INVENTION

It is therefore an object of the present invention to eliminate the defect in the prior art.

It is another object of the present invention to provide a fine pattern test apparatus using a picture image processing method in which any model pattern can be modified to be analogous to practical test target patterns regardless of the original form thereof to thereby make precise comparison testing possible for any test target pattern.

The foregoing objects of the invention are attained by a method in which the content of the center picture element 23 is decided to be "0" or "1" on the basis of the ratio of the number of picture elements the contents of which take the value of "0" to the number of picture elements the contents of which take the value of "1" in all the picture elements contained in an arrangement 21 of N×N picture elements as shown in FIG. 1, inclusive of picture elements located in the inner portion of the arrangement 21 as well as inclusive of picture elements located in the outer peripheral portion thereof. In the case where the content of a picture element is "1", the picture element is defined to be a patterned picture element. On the other hand, in the case where the content of a picture element is "0", the picture element is defined to be a non-patterned picture element. (It is a matter of course that the definitions may be reversed.)

In this invention, picture elements used to decide the value ("0" or "1") of the center picture element exist over the whole plane of a picture element area containing the center picture element. Accordingly, even in the case where the model pattern has been rounded as shown in FIG. 2C, the pattern can be reformed to be very analogous to the test target pattern. Accordingly, the comparison test for the target pattern can be carried out regardless of the form of the model pattern of designed data or mask, so that misjudgment as to whether the test target pattern is good or not can be reduced.

DESCRIPTION OF THE PREFERRED EMBODIMENTS

Figure 4:
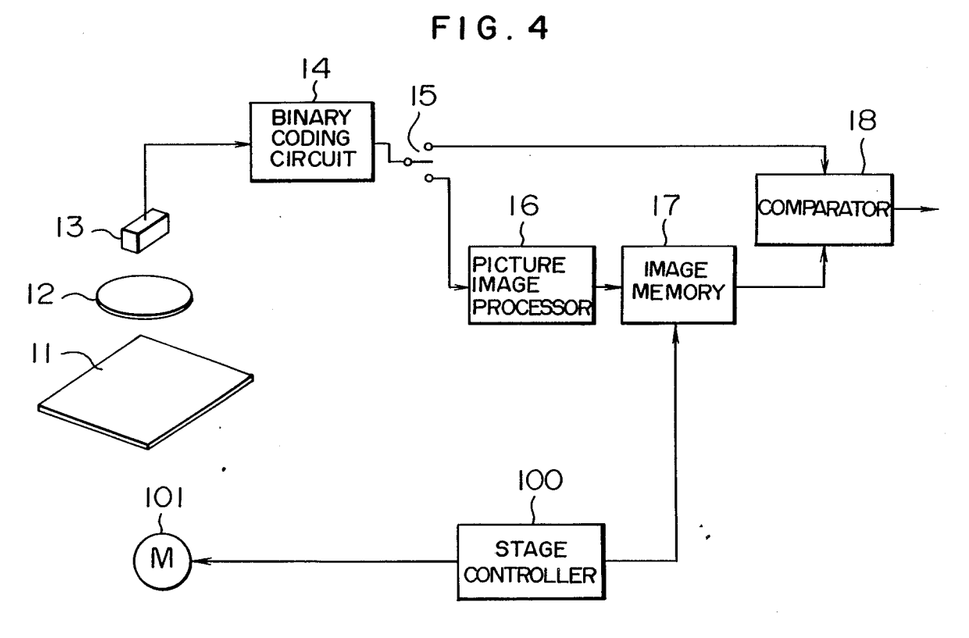
FIG. 4 is a block diagram showing the construction of an embodiment of the fine pattern test apparatus according to the present invention.

FIG. 4 is a block diagram showing an embodiment of the pattern test apparatus according to the present invention. For example, this embodiment is directed to a pattern test apparatus using a photomask as a model pattern. An image of a reference matter (target of measurement) 11 as a photomask provided with a model pattern is formed on a sensor 13 through a imaging lens 12. The picture image information obtained by the sensor 13 is converted into binary data by a binary-coding circuit 14. In this case where such a model pattern is to be inputted, a switch 15 is switched so as to be connected to a picture image processing circuit 16. In this case, the binary data is processed by the picture image processing circuit 16 so as to be analogous to the test target pattern, and then the processed binary data is stored in an image memory 17.

On the other hand, the test target pattern is inputted into the sensor 13 and then converted into binary data by the binary-coding circuit 14 in the same manner as described above. In the case where the test target pattern is inputted, the switch 15 is connected directly to a comparator circuit 18. In the comparator circuit 18, the binary data of the test target pattern are compared with the data stored in the image memory 17 to thereby discriminate fault data.

A stage controller 100 controls a motor 101 to move a stage (not shown) on which the target 11 of the test is mounted to thereby carry out the test for a part or whole of the test target 11. Further, the stage controller 100 operates the image memory 17 synchronously with the motion of the stage so that exact comparison can be made between a picture element of the test target pattern and corresponding one of the model patterns.

Figure 5:
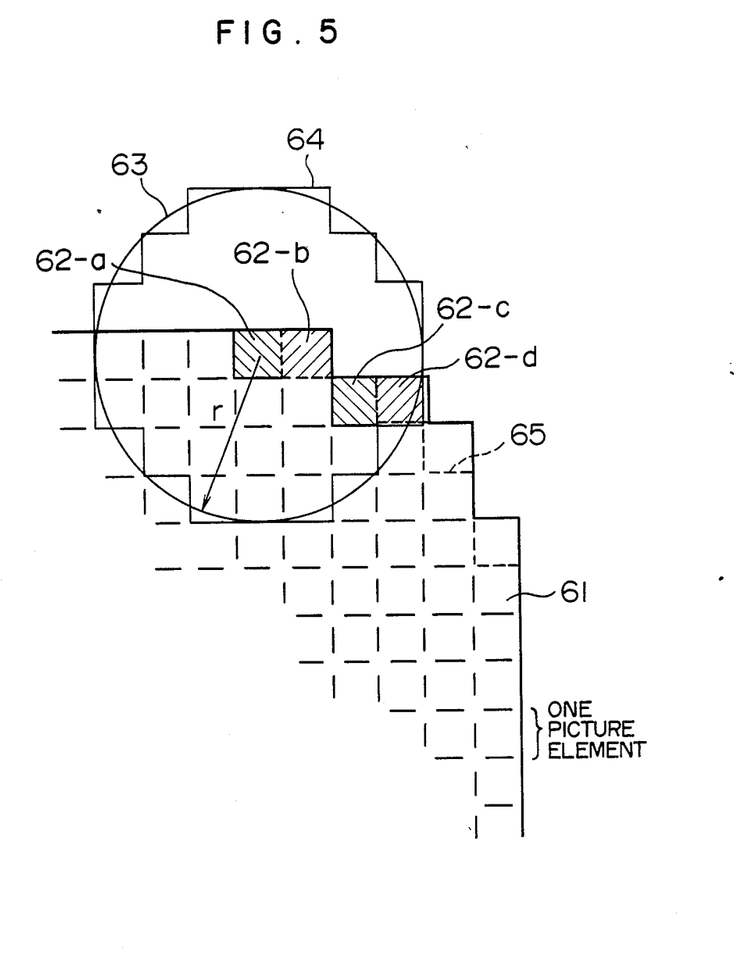
FIG. 5 is a view for explaining a picture image processing technique according to the present invention.

An example of picture image processing carried out in the picture image processing circuit is shown in FIG. 5. It is now considered that a picture element 62-a is selected from all picture elements of a data pattern containing a model pattern 61 of a photomask and that a picture element area 64 is determined to be contained in a circle 63 with radius r drawn around the selected picture element 62-a. Within the picture element area, the number of picture elements in which the contents X take the value of "1" is compared with the number of picture elements in which the contents X take the value of "0". When the number of picture elements of "1" is larger than the number of picture elements of "0", the center picture element 62-a is decided to be "1". On the other hand, when the number of picture elements of "0" is larger than the number of picture elements of "1", the center picture element 62-a is decided to be "0". The aforementioned center picture element 62-a is applied onto all the picture elements of the data pattern to carry out the same processing, successively. FIG. 5 shows the case where the picture element area is contained in a circle with radius r(=3.5). Particularly in FIG. 5, 17 picture elements of "0" and 20 picture elements of "1" are contained in the picture element area 64, so that the center picture element 62-a is decided to be "1" because the picture elements of "1" are larger in number than those of "". The aforementioned center picture element 62-a is applied onto all the picture elements to carry out the same processing, successively. Accordingly, the picture element 62-b is decided to be "0", the picture element 62-c is decided to be "1", and the picture element 62-d is decided to be "0". Consequently, the pattern form 61 is reformed so as to be rounded at its corner portion as shown by the broken line 65.

A desired extent of corner rounding given though the aforementioned processing can be established by changing the radius r of the circle.

Figure 6:
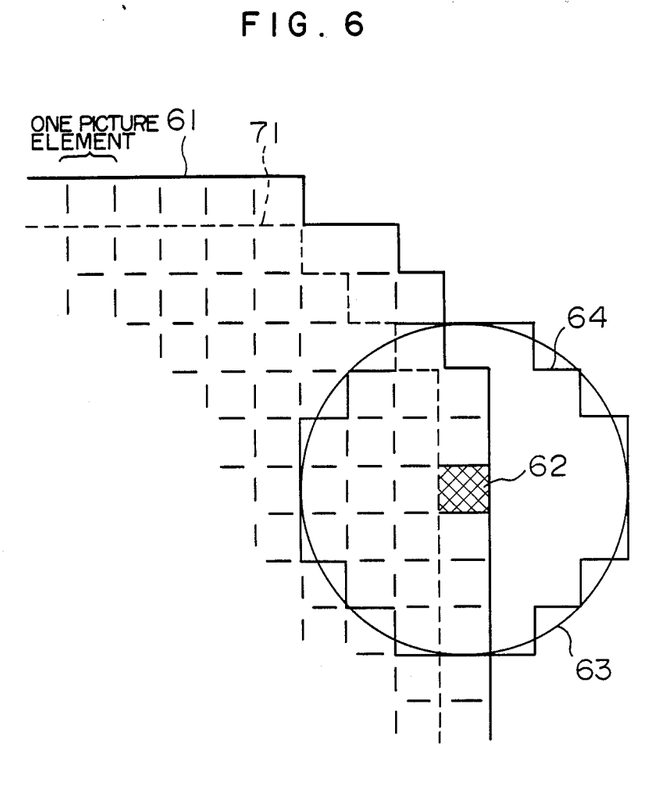
FIG. 6 is a view for explaining a line thinning action fulfilled by the picture image processing technique according to the present invention.

Further, FIG. 6 shows the case where the pattern form must be changed to make the line width thereof thick or thin. The ratio of the number of the picture elements of "1" to the number of the picture elements of "0" within a picture element area 64 contained in a circle 63 with radius r is suitably predetermined other than the ratio 1:1. Assuming now that the center picture element 62 is decided to be "1" when the number of the picture elements of "1" within the picture element area 62 of the model pattern of FIG. 6 contained in the circle 63 with radius r(=3.5) are not smaller than 24, and that the center picture element 62 is decided to be "0" when the number of the picture elements of "0" within the picture element area 62 are not smaller than 14, the model pattern 61 can be modified in the form 71 of a thinned line.

According to this embodiment, the designed data pattern or mask pattern can be modified in accordance with the fact that corner rounding or line thickening (thinning) occurs in the process of producing a printed board. Accordingly, precise comparison test for the fine pattern of such a printed board or the like can be carried out by use of the modified fine pattern.

Although this embodiment has shown the case where the picture element area 64 is contained in a circle 63 with radius r, it is to be understood that the area contained in such a circle is merely used as an example to carry out the picture image processing isotropically to thereby attain a uniform effect regardless of the direction of the pattern. It is to be appreciated that the area may be determined by any figure except and is not limited to a circle, as long as the figure used can define one area.

Although the input model pattern of FIG. 4 is formed of a photomask or the like detected by the sensor 13, the model pattern may be formed of designed data as another embodiment shown in FIG. 9 with respect to which description will be made later.

Figure 7:
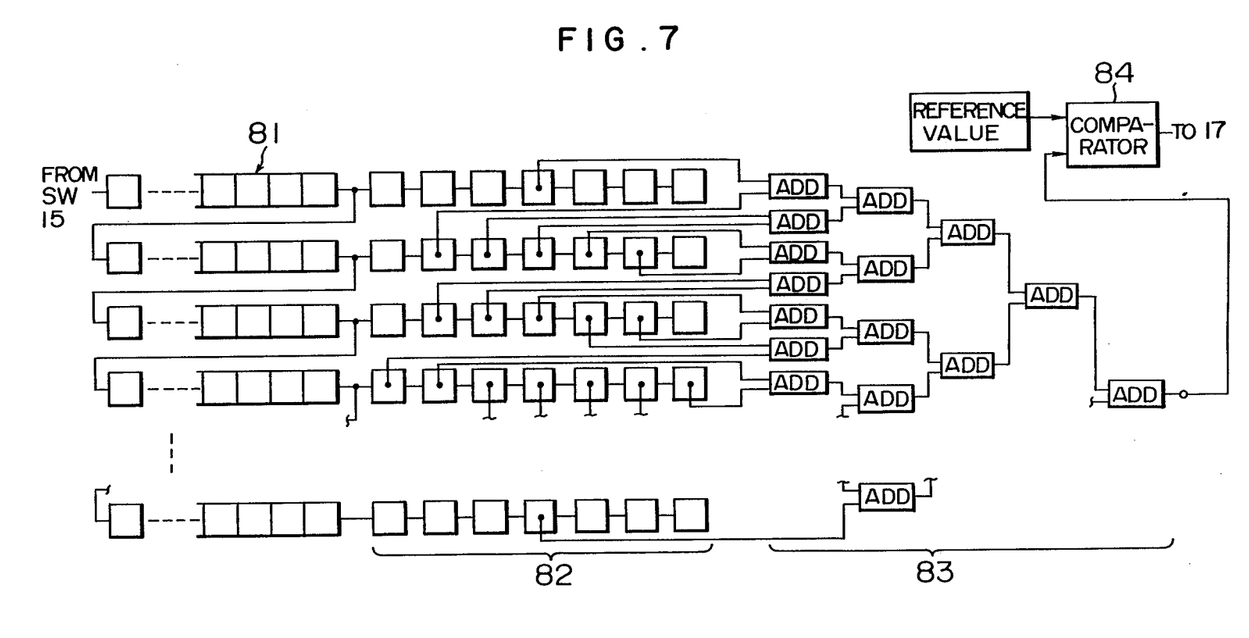
FIG. 7 is a view showing a first specific example of the picture image processing circuit according to the invention.

FIG. 7 shows a specific example of the picture image processing circuit 16.

The pattern signal from the binary-coding circuit 14 is fed to a shift register array 81, and successively fed to a picture image selecting circuit 82 composed of a plurality of latches. Picture element data selected by the picture image selecting circuit 82 corresponding to the designated area such as a circle, a square or the like are fed to an adding circuit 83 composed of a plurality of adders (ADDs) to thereby generate a result of addition. The result of addition is compared with a preset reference numerical value by a comparator 84, so that the value of the center picture element 62 is decided based on the result of comparison.

Figure 8:
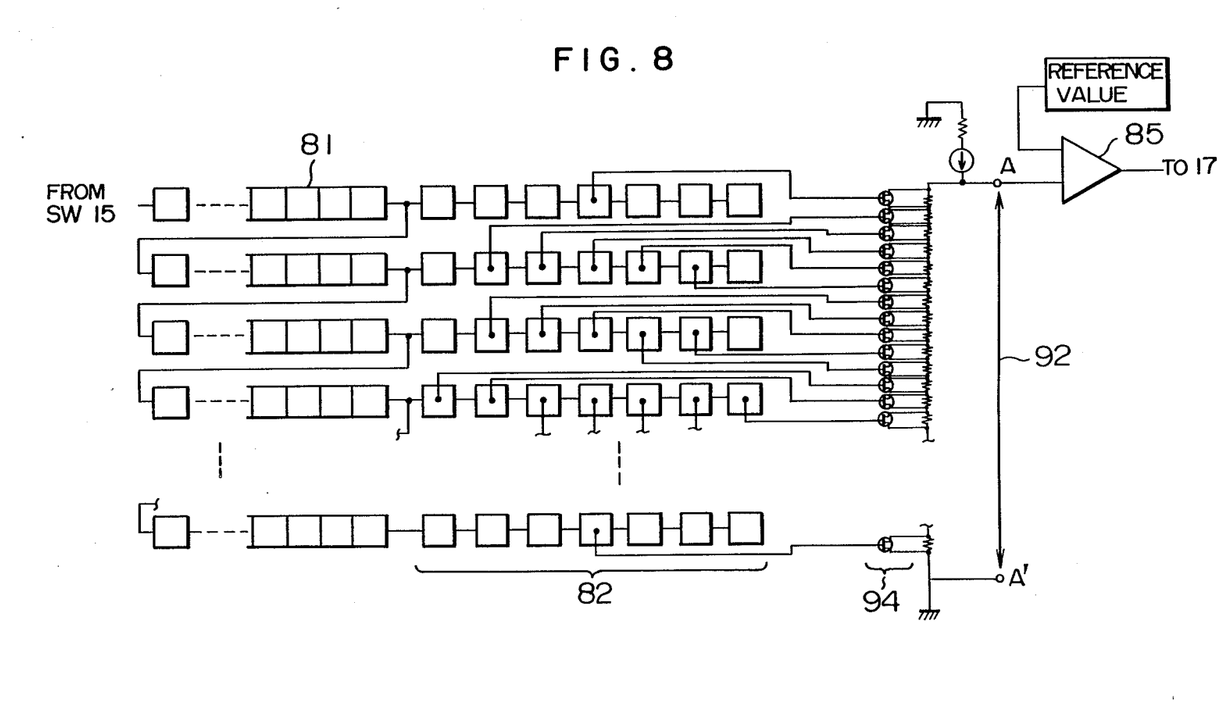
FIG. 8 is a view showing a second specific example of the picture image processing circuit according to the present invention.

FIG. 8 shows another specific example of the picture image processing circuit 16.

In FIG. 8, an analog switch 94 is closed by the number of picture elements of "1" corresponding to the picture element data selected by the picture image selecting circuit 82 in the same manner as described above with reference to FIG. 7, so that the voltage level between terminals A and A' is determined. The voltage level 92 is compared with a reference voltage value preset in a comparator 85, so that the value of the center picture element 62 is decided based on the result of comparison.

Figure 9:
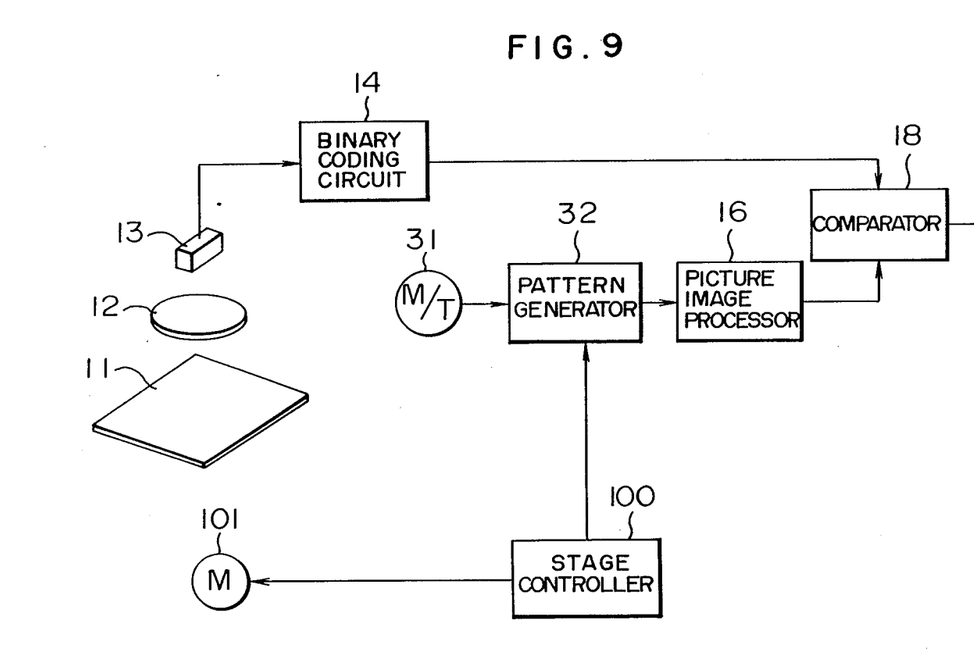
FIG. 9 is a block diagram showing another embodiment of the fine pattern test apparatus according to the present invention.

FIG. 9 is a block diagram showing another embodiment of the pattern test apparatus according to the present invention. In FIG. 9, parts the same as or equivalent to those in FIG. 4 are referenced correspondingly, and the description of those parts will be omitted.

Designed data to form model patterns are recorded on a tape 31. The data of the tape 31 are reformed as a binary-coded data pattern by a pattern generating circuit 32. The binary-coded data pattern is fed to the picture image processing circuit 16. The data pattern is processed by the picture image processing circuit 16 in the same manner as described above with reference to FIG. 4, so that the thus processed model pattern is fed to the comparator circuit 18. On the other hand, the image of the test target 11 as a test target pattern is formed on the sensor 13 through the imaging lens 12. The picture image information obtained by the sensor 13 is converted into binary data by the binary-coding circuit 14, and then fed to the comparator circuit 18. In the comparator circuit 18, the binary data of the test target pattern are compared with the data of the processed model pattern to thereby discriminate a fault.

According to the invention, a test apparatus in which misjudgment is reduced in the fine pattern test for printed boards or the like can be provided.

What is claimed is:

1. An apparatus for testing a testing circuit pattern, comprising:
    an imaging means for detecting an image signal by scanning a photo-image of the testing circuit pattern;
    a binary coding circuit for converting said image signal to a binary picture element signal;
    a reference binary pattern generating means for generating a reference binary pattern signal in synchronism with said scanning;
    processing means, including a picture image selecting means for selecting a picture element area having a desired dimension from said reference binary pattern signal, an adding means for calculating a sum of all of binary picture element signals derived from said selected picture element area and a comparing means for comparing the sum with a predetermined reference value and giving a reference binary picture element signal obtained by the comparison to a center picture element of said picture element area so that said center picture element is reformed to be substantially analogous to the binary picture element signal of the testing circuit pattern; and
    means for detecting a defect by comparing said binary picture element signal with said reference binary picture element signal for preventing misjudgment of the corner of said testing circuit pattern.

2. An apparatus according to claim 1, in which said picture element area is defined by a circle with a predetermined radius.

3. An apparatus according to claim 1, in which said reference binary pattern generating means includes a magnetic tape device carrying pattern designating data recorded thereon.

4. A method for testing a testing circuit pattern, comprising the steps of:
    detecting image signals by scanning a photo-image of the testing circuit pattern;
    converting said image signals to binary picture element signals;
    generating reference binary pattern signals in synchronism with said scanning;
    selecting from said reference binary pattern signals, a picture element area having a desired dimension;
    calculating a sum of all of said binary picture element signals derived from said selected picture element area;
    comparing the sum with a predetermined reference value in order to produce a reference binary picture element signal;
    passing the reference binary picture element signal obtained by the comparison to a center picture element of said picture element area so that said center picture is reformed to be substantially analogous to the binary picture element signal of the testing circuit pattern; and
    comparing said binary picture element signal with said reference binary picture element signal for preventing misjudgment of the corner of said testing circuit pattern.

5. A pattern test apparatus for testing circuit patterns which have a corner portion thereof rounded over several picture elements the apparatus comprising:
    an imaging means for detecting image signals by scanning a photo-image of the testing circuit pattern;
    a binary coding circuit for converting said image signals to binary picture element signals;
    a reference binary pattern generating means for generating a reference binary pattern signal in synchronism with said scanning;
    a processing means, said processing means including picture image selecting means for selecting from said reference binary pattern signal a picture element area having a desired dimension,
    adding means for calculating a sum of all of binary picture element signals derived from said selected picture element area, and
    comparing means for comparing the sum with a predetermined reference value to pass a reference binary picture element signal obtained by the comparison to a center picture element of said picture element area so that said center picture element is reformed to be substantially analogous to the binary picture element signal of the testing circuit pattern; and
    means for detecting a defect by comparing said binary picture element signal with said reference binary picture element signal for preventing misjudgment of the testing circuit pattern.

* * * * *

UNITED STATES PATENT AND TRADEMARK OFFICE
CERTIFICATE OF CORRECTION

PATENT NO. : 4,962,541

DATED : October 9, 1990

INVENTOR(S) : Hideaki Doi, et al.

It is certified that error appears in the above-identified patent and that said Letters Patent is hereby corrected as shown below:

Claim 4, column 6, line 35, after "center picture" and before "is", please insert --element--.

Signed and Sealed this

Thirty-first Day of December, 1991

*Attest:*

HARRY F. MANBECK, JR.

*Attesting Officer*     *Commissioner of Patents and Trademarks*